United States Patent
Yenkar et al.

(10) Patent No.: US 10,888,524 B2
(45) Date of Patent: Jan. 12, 2021

(54) IMMEDIATE RELEASE TABLET OF DOFETILIDE

(71) Applicant: Enaltec Pharma Research Pvt. Ltd., Thane (IN)

(72) Inventors: Piyush S. Yenkar, Thane (IN); Alok Tripathi, Thane (IN); Vilas Jadhav, Thane (IN); Amit Manmode, Thane (IN)

(73) Assignee: ENALTEC PHARMA RESEARCH PVT. LTD., Thane (IN)

( * ) Notice: Subject to any disclaimer, the term of this patent is extended or adjusted under 35 U.S.C. 154(b) by 0 days.

(21) Appl. No.: 16/045,447

(22) Filed: Jul. 25, 2018

(65) Prior Publication Data
US 2019/0240158 A1 Aug. 8, 2019

(30) Foreign Application Priority Data
Feb. 5, 2018 (IN) .............................. 201821004230

(51) Int. Cl.
*A61K 9/20* (2006.01)
*A61K 9/28* (2006.01)
*A61K 31/18* (2006.01)

(52) U.S. Cl.
CPC .......... *A61K 9/2054* (2013.01); *A61K 9/2009* (2013.01); *A61K 9/2013* (2013.01); *A61K 9/2027* (2013.01); *A61K 9/2095* (2013.01); *A61K 9/28* (2013.01); *A61K 31/18* (2013.01)

(58) Field of Classification Search
CPC ............. A61K 9/20; A61K 9/28; A61K 31/18
See application file for complete search history.

(56) References Cited

U.S. PATENT DOCUMENTS

| 4,959,366 A | 9/1990 | Cross et al. |
| 2001/0033859 A1 | 10/2001 | Selzer |
| 2002/0098232 A1* | 7/2002 | Midha .................. A61K 9/2081 424/457 |

FOREIGN PATENT DOCUMENTS

EP 0965341 A2 12/1999

OTHER PUBLICATIONS

Kousar Begum et al., *J. Pharma. Res.* 2017, 6(8):108-114.

* cited by examiner

*Primary Examiner* — Zohreh A Fay
(74) *Attorney, Agent, or Firm* — Blank Rome LLP

(57) ABSTRACT

The present invention encompasses immediate release tablets of dofetilide, methods of treatment with them, as well as a process for manufacturing the same.

9 Claims, 1 Drawing Sheet

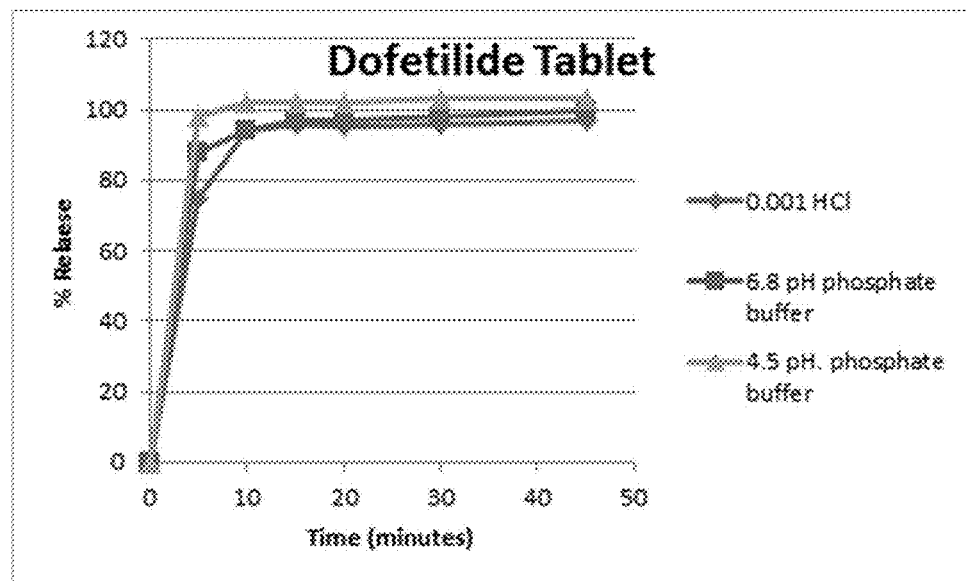
Figure 1: Dissolution of Dofetilide tablet 0.5 mg
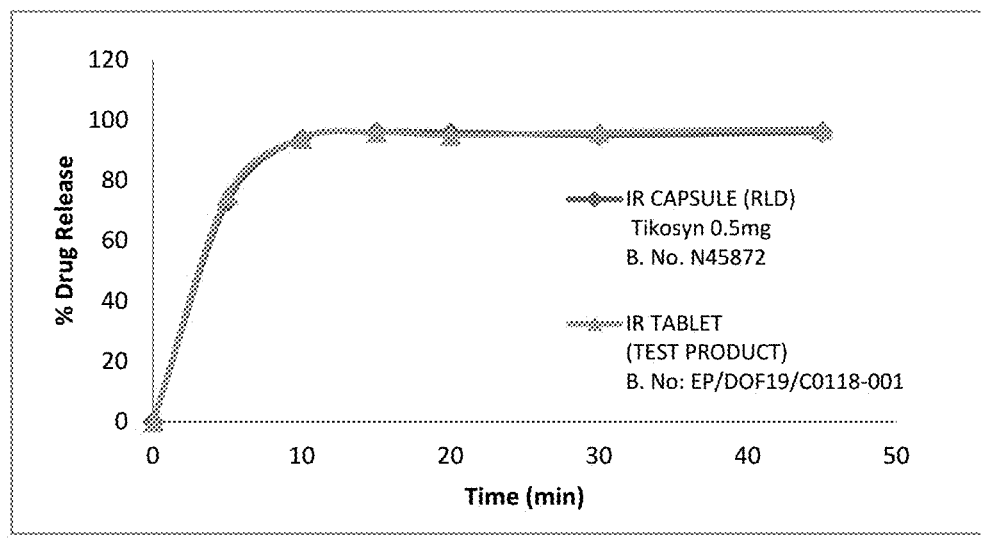
Figure 2: Dissolution Comparison of Dofetilide IR Capsules (RLD), and IR Tablets (Test Product)

IMMEDIATE RELEASE TABLET OF DOFETILIDE

This application claims the benefit of Indian Patent Application No. 201821004230, filed on Feb. 5, 2018, the entirety of which is hereby incorporated by reference herein.

FIELD OF THE INVENTION

The present invention is directed to immediate release tablets of dofetilide, methods of treatment with them, as well as a process for manufacture thereof.

BACKGROUND OF THE INVENTION

Dofetilide is designated chemically as N-[4-[2-[methyl[2-[4-[(methylsulfonyl)amino]phenoxy]ethyl]amino]ethyl]phenyl]-methane sulfonamide with an empirical formula of $C_{19}H_{27}N_3O_5S_2$ and a molecular weight of 441.6.

Dofetilide is described in U.S. Pat. No. 4,959,366 and is represented by structural formula I:

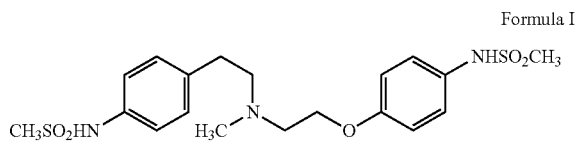

Formula I

U.S. Pat. No. 4,959,366 discloses certain [N-alkyl-N-(nitro-, alkylsulphonamido, or amino-phenalkyl)amino]-alkyl, alkoxy, or alkylthio phenyl derivatives having utility as anti-arrhythmic agents.

Dofetilide is a selective inhibitor of the rapid component of the delayed rectifier potassium current which prolongs the action potential duration and the effective refractory period in a concentration dependent manner. Clinical studies have demonstrated that dofetilide is effective in treating patients with atrial as well as ventricular arrhythmias. Specifically, for example, Dofetilide has been studied in patients with severe left ventricular dysfunction (William M. Bailey et al., Electrophysiologic and Hemodynamic Effects of Dofetilide in Patients with Severe Left Ventricular Dysfunction, Circulation, 1992, Vol. 86, Part 4, Supplement 1, page 1265) in which it was found that, unlike class I agents, Dofetilide is safe in patients with congestive heart failure.

Dofetilide is commercially available in the United States in the form of 0.125, 0.25, and 0.5 mg hard gelatin capsules, under the trade name Tikosyn® and is indicated for the maintenance of normal sinus rhythm (delay in time to recurrence of atrial fibrillation/atrial flutter [AF/AFl]) in patients with atrial fibrillation/atrial flutter of greater than one week duration who have been converted to normal sinus rhythm. Tikosyn is also indicated for the conversion of atrial fibrillation and atrial flutter to normal sinus rhythm.

U.S. Publication No. 2001/0033859 discloses a dofetilide-containing transdermal therapeutic system in plaster form with a backing layer which is impermeable to active ingredient, with an active ingredient reservoir which is connected thereto, with a contact adhesive layer and with a protective layer which can be detached before application.

Kousar Begum et al., J. Pharma. Res. 2017, 6(8):108-114, discloses a pulsatile drug delivery system of dofetilide.

European Publication No. 0965341 A2 discloses pharmaceutical compositions comprising dofetilide and a calcium channel blocker.

Tablets are the most cost-effective supplements in general because they are less-expensive to manufacture than other formats. Tablets allow the manufacturer to pack the most material into a given space. From the manufacturing standpoint, tablets are the most shelf-stable choice and retain their potency over a longer time than liquids, powders and most capsules.

Tablets can also be made in the widest variety of shapes and sizes, offering even more flexibility and options for the manufacturer and the consumer.

Scored tablet makes dose splitting possible.

Accordingly, there is a continuing need in the industry for tablets which is cost effective, easy for swallowing and more stable.

SUMMARY OF THE INVENTION

A first aspect of the present invention is an immediate release tablet formulation comprising dofetilide or a pharmaceutically acceptable salt thereof.

Another aspect is an immediate release tablet formulation comprising dofetilide or a pharmaceutically acceptable salt thereof and optionally a coating.

In one embodiment, the immediate release tablet formulation is bioequivalent to dofetilide capsule marketed under the brand name 'Tikosyn®'.

Another aspect is a method for preparing an immediate release tablet formulation comprising dofetilide or a pharmaceutically acceptable salt thereof.

Another aspect of the present invention is to provide pharmaceutical tablets in a unit pack which improves the ease of handling, transportation, administration and patient compliance.

Another embodiment is an immediate release tablet formulation comprising dofetilide or a pharmaceutically acceptable salt thereof, one or more binders and/or diluents, one or more disintegrants, one or more glidants and/or lubricants, and optionally a coating.

Another embodiment is an immediate release tablet formulation free of binder comprising dofetilide or a pharmaceutically acceptable salt thereof, one or more diluents, one or more disintegrants, one or more glidants and/or lubricants, and optionally a coating.

Yet another aspect is an immediate release tablet formulation comprising:
a) dofetilide or a pharmaceutically acceptable salt thereof;
b) at least one pharmaceutically acceptable diluent selected from lactose, microcrystalline cellulose, dextrose, sucrose, maltodextrin, saccharose, starch, mannitol or sorbitol and dibasic calcium phosphate;
c) at least one pharmaceutically acceptable binder selected from acacia, alginic acid, alginates, agar, calcium carrageenan, sodium carboxymethylcellulose, microcrystalline cellulose, dextrin, ethylcellulose, gelatin, guar gum, povidone, glucose syrup, hydroxyethylcellulose, hydroxypropylcellulose, hydroxypropylmethylcellulose, pectin, polyethylene glycol, pregelatinized starch or carboxymethylcellulose;
d) at least one pharmaceutically acceptable disintegrant selected from alginic acid, alginates, cellulose, cellulose derivatives, croscarmellose sodium, crospovidone, polacrillin potassium, sodium starch glycolate, starch, carboxymethyl starch or pregelatinized starch;
e) at least one glidant selected from colloidal silicon dioxide, talc or corn starch and/or at least one lubricant selected from sodium stearyl fumarate (SSF), magnesium stearate, corn starch, glyceryl behneate, zinc stearate, calcium stearate, stearic acid or hydrogenated vegetable oil; and
f) optionally a coating.

Another aspect is an immediate release tablet formulation comprising:
a) dofetilide or a pharmaceutically acceptable salt thereof;
b) at least one pharmaceutically acceptable diluent in an amount ranging from about 5% to about 98% weight/weight (% w/w), such as about 70% to about 97% w/w or about 90% to about 95% w/w;
c) at least one pharmaceutically acceptable binder in an amount ranging from about 0.02% to about 90% w/w and more preferably from about 0.02 to about 20% w/w;
d) at least one pharmaceutically acceptable disintegrant in an amount ranging from about 1% to about 30% w/w and more preferably from about 1% to about 20% w/w;
e) at least one glidant and/or at least one lubricant; and
f) optionally a coating.

Another aspect is an immediate release tablet formulation, preferably free of binder, comprising:
a) dofetilide or a pharmaceutically acceptable salt thereof;
b) diluent comprising microcrystalline cellulose in an amount ranging from about 5% to about 98% w/w, such as about 70% to about 97% w/w or about 90% to about 95% w/w;
c) disintegrant comprising croscarmellose sodium in an amount ranging from about 1% to about 30% w/w and more preferably from about 1% to about 20% w/w;
d) glidant comprising colloidal silicon dioxide in an amount ranging from about 0.07% to about 3% and/or lubricant comprising magnesium stearate in an amount ranging from about 0.1% to about 3%; and
e) optionally a coating comprising functional or non-functional coating.

Another aspect is an immediate release tablet formulation comprising:
a) dofetilide or a pharmaceutically acceptable salt thereof;
b) diluent comprising microcrystalline cellulose in an amount ranging from about 5% to about 98% w/w, such as about 70% to about 97% w/w or about 90% to about 95% w/w;
c) binder comprising povidone or/and hydroxypropyl methylcellulose (HPMC) in an amount ranging from about 0.02-30% w/w %, and more preferably 0.02-20% w/w;
d) disintegrant comprising croscarmellose sodium in an amount ranging from about 1% to about 30% w/w and more preferably from about 1% to about 20% w/w;
e) glidant comprising colloidal silicon dioxide in an amount ranging from about 0.07% to about 3% and/or lubricant comprising magnesium stearate in an amount ranging from about 0.1% to about 3%; and
f) optionally a coating comprising functional or non-functional coating.

Another aspect is a dofetilide immediate release tablet composition, preferably free of binder, comprising:
a) dofetilide or a pharmaceutically acceptable salt thereof in an amount in the range of 0.05 to about 10% w/w (based on 100% total weight of the tablet), such as from about 0.1 to about 2%, from about 0.1 to about 1%, from about 0.1 to about 0.5%, or from about 0.1 to about 0.3%;
b) diluent comprising microcrystalline cellulose in an amount ranging from about 5% to about 98% w/w, such as about 70% to about 97% w/w or about 90% to about 95% w/w;
c) disintegrant comprising croscarmellose sodium in an amount ranging from about 1% to about 30% w/w and more preferably from about 1% to about 20% w/w;
d) glidant comprising colloidal silicon dioxide in an amount ranging from about 0.07% to about 3% and/or lubricant comprising magnesium stearate in an amount ranging from about 0.1% to about 3%; and
e) optionally a coating comprising functional or non-functional coating.

Another aspect is a dofetilide immediate release tablet composition comprising:
a) dofetilide or a pharmaceutically acceptable salt thereof in an amount in the range of 0.05 to about 10% w/w (based on 100% total weight of the tablet), such as from about 0.1 to about 2%, from about 0.1 to about 1%, from about 0.1 to about 0.5%, or from about 0.1 to about 0.3%;
b) diluent comprising microcrystalline cellulose in an amount ranging from about 5% to about 98% w/w, such as about 70% to about 97% w/w or about 90% to about 95% w/w;
c) binder comprising povidone or/and HPMC in an amount ranging from about 0.02-30% w/w %, and more preferably 0.02-20% w/w;
d) disintegrant comprising croscarmellose sodium in an amount ranging from about 1% to about 30% w/w and more preferably from about 1% to about 20% w/w;
e) glidant comprising colloidal silicon dioxide in an amount ranging from about 0.07% to about 3% and/or lubricant comprising magnesium stearate in an amount ranging from about 0.1% to about 3%; and
f) optionally a coating comprising functional or non-functional coating.

Another aspect is a method for preparing an immediate release tablet formulation comprising dofetilide or a pharmaceutically acceptable salt thereof, wherein the process comprises direct compression, dry granulation, wet granulation, a fluidized technique (such as the use of a fluidized bed), or extrusion spheronization (such as extrusion spheronization using multiparticulates).

Another aspect is a method for manufacturing an immediate release tablet containing dofetilide or a pharmaceutically acceptable salt thereof, a diluent, a disintegrant, a glidant, and a lubricant comprises:
a) adding a first portion of diluent to dofetilide or a pharmaceutically acceptable salt thereof and then adding a second portion of the diluent to form a first mixture;
b) mixing the first mixture;
c) mixing a third portion of the diluent, the disintegrant, and the glidant to form a second mixture;
d) adding a first portion of the second mixture to the first mixture and then adding the remaining portion of the second mixture to form a third mixture;
e) mixing the third mixture;
f) lubricating the third mixture by addition of a lubricant;
g) compressing the lubricated mixture into a tablet; and
h) optionally coating the tablet, wherein the coating comprises functional or non-functional coating.

Another aspect is a method for manufacturing dofetilide immediate release tablet comprises:

a) dry mixing dofetilide or a pharmaceutically acceptable salt thereof and one or more pharmaceutically acceptable excipients;

b) dissolving (e.g., with stirring until a clear solution is obtained) one or more binders in an aqueous solvent or non-aqueous solvent or mixture thereof (e.g., a mixture of water and isopropanol (IPA)) to form a binder solution;

c) granulating the blend of step a) with the binder solution of step b);

d) drying the granulation product of step c), and subsequently classify the granules (e.g., sifting the granules);

e) lubricating the granules of step d);

f) compressing the mixture of step e) into tablet (e.g., using round/capsule/oval shaped punches and optionally with a score line for dose adjustment).

Another aspect is a dofetilide immediate release tablet formulation containing total impurities less than 1.5% (based on 100% total weight of the tablet) at accelerated stability conditions (i.e., storage at a temperature of 40° C. and a relative humidity 75%) for 1, 2, 3, or 6 months.

In one embodiment, the dofetilide immediate release tablet formulation is free of binder.

The tablets described herein may be scored (e.g., a tablet including a single score line delineating two equal halves containing equal amounts of dofetilide (or a pharmaceutically acceptable salt thereof)). The scoring permits the tablet to be divided at the score line when a force is applied to the score line, such as with a knife. Scored tablets make dose splitting possible. A scored tablet includes a groove called a "score line" on the surface of the tablet. The purpose of providing the score line is to enable a tablet to be easily divided by applying a force to the tablet by a human in order to adjust the dose.

Another aspect is a scored tablet of dofetilide which provides dose flexibility, ease of swallowing and may reduce the costs of medication.

Patients may have more difficulty in swallowing a capsule than a tablet because the floating property of the capsule makes it lighter than water, causing the uneasy globus sensation. In contrast, tablets are typically heavier than water, which minimizes the uneasy feeling in the oral cavity when swallowing. Thus, the tablet formulation may alleviate patient discomfort, leading to increased compliance, better quality of life, and better efficacy.

Another aspect is a process of preparing an immediate release tablet formulation comprising dofetilide or a pharmaceutically acceptable salt thereof.

Yet another aspect is a method of treating an arrhythmia, such as atrial fibrillation, in a mammal (e.g., a human, either male or female) in need of such treatment comprising administering to the mammal a therapeutically effective amount of a tablet formulation of the present invention. One embodiment is a method for maintenance of normal sinus rhythm (delay in time to recurrence of atrial fibrillation/atrial flutter [AF/AFl]) in a human patient with atrial fibrillation/atrial flutter of greater than one week duration who has been converted to normal sinus rhythm comprising administering to the patient an effective amount of a tablet formulation of the present invention. Another embodiment is a method for the conversion of atrial fibrillation and/or atrial flutter to normal sinus rhythm in a human patient comprising administering to the patient an effective amount of a tablet formulation of the present invention. Administration of the tablet formulation includes dividing a scored tablet of the present invention and administering one or more divided portions of the tablet. Administration of the tablet formulation also includes administering one or more tablets of the present invention or divided portions thereof or a combination thereof.

BRIEF DESCRIPTION OF THE FIGURE

FIG. 1 depicts the dissolution of a 0.5 mg dofetilide tablet of Example 1 according to USP Type I (basket) at 100 rpm in 900 mL of (i) 0.001 M HCl, (ii) phosphate buffer at pH 6.8, or phosphate buffer at pH 4.5.

FIG. 2 depicts the dissolution of (a) a 0.5 mg Tikosyn® immediate release dofetilide capsule, and (b) the immediate release 0.5 mg dofetilide tablet of Example 1 according to USP Type I (basket) at 100 rpm in 900 mL of 0.001 M HCl.

DETAILED DESCRIPTION OF THE INVENTION

The present invention provides an immediate release tablet formulation comprising dofetilide or a pharmaceutically acceptable salt thereof. In general, the tablet formulation includes one or more pharmaceutically acceptable excipients. The dofetilide or a pharmaceutically acceptable salt thereof can be in any form (preferably a solid state form), such as an amorphous, anhydrous, solvate, or hydrate form.

The immediate release tablet formulation according to the present invention provides immediate release of dofetilide or a pharmaceutically acceptable salt thereof. In this regard, "immediate release" herein refers to dissolution of at least 80 wt. %, more preferably at least 85 wt. % of dofetilide or a pharmaceutically acceptable salt thereof from the tablet within 15 minutes as measured according to USP Type I (basket) at 100 rpm in 900 mL of 0.001 M HCl. The tablet meets the USP dissolution specifications for immediate release capsule containing dofetilide.

The dofetilide used in the present invention may be crystalline dofetilide, such as polymorphic form P162, P162a, P143, P162b, P136 or a mixture thereof. These polymorphic forms are described in U.S. Pat. No. 6,124,363, which is hereby incorporated by reference. In one preferred embodiment, the tablet includes dofetilide in P162 form which is reported in U.S. Pat. No. 6,124,363.

The tablet formulations may contain a combination of excipients and may be manufactured using a method that provides content uniformity, desirable tensile strength and suitable disintegration and dissolution times.

Preferred tablet properties include one or more of the following: a tensile strength of at least about 2 MPa (megapascal), a disintegration time not more than 15 minutes, a hardness of 300±50 N, a percent friability of not more than 1%, and a dissolution exceeding 80% after 30 minutes.

One embodiment is an immediate release tablet formulation that comprises dofetilide or a pharmaceutically acceptable salt thereof, one or more binders and/or diluents, one or more disintegrants, one or more glidants and/or lubricants, and optionally a coating.

Another embodiment is an immediate release tablet formulation free of binder that comprises dofetilide or a pharmaceutically acceptable salt thereof, one or more diluents, one or more disintegrants, one or more glidants and/or lubricants, and optionally a coating.

The preferred amount of dofetilide or a pharmaceutically acceptable salt thereof is in the range of from about 0.05 to about 10% w/w (based on 100% total weight of the tablet), such as from about 0.1 to about 2%, from about 0.1 to about 1%, from about 0.1 to about 0.5%, or from about 0.1 to about 0.3%. The most preferred amounts of Dofetilide is 0.1 mg and 5 mg and the most preferred amount is in the range of 0.1 mg to 0.5 mg.

Suitable pharmaceutically acceptable diluents include, but are not limited to, lactose (e.g., lactose monohydrate), microcrystalline cellulose, dextrose, sucrose, maltodextrin, saccharose, starch, mannitol, sorbitol, dibasic calcium phosphate, or any combination of any of the foregoing.

Preferred diluents include microcrystalline cellulose, lactose monohydrate, dibasic calcium phosphate, starch, or any combination of any of the foregoing.

The diluent may be present in an amount ranging from about 5%-98% w/w, based upon 100% total weight of the tablet, such as from about 90 to about 98% w/w or from about 92 to about 97% w/w. In one embodiment, the amount of diluent is from about 94 to about 95% w/w.

Suitable pharmaceutically acceptable binders include, but are not limited to, acacia, alginic acid, alginates, agar, calcium carrageenan, sodium carboxymethylcellulose, microcrystalline cellulose, dextrin, ethylcellulose, gelatin, guar gum, povidone, glucose syrup, hydroxyethylcellulose, hydroxypropylcellulose, hydroxypropylmethylcellulose, pectin, polyethylene glycol, pregelatinized starch, carboxymethylcellulose, or any combination of any of the foregoing.

Preferred binders include, but are not limited to, hydroxypropylmethylcellulose, povidone, or any combination of any of the foregoing.

The binders may be present in an amount ranging from about 0.02% to about 98% w/w (based upon 100% total weight of the tablet), such as from about 0.02% to about 60% w/w, from about 0.02% to about 25% w/w, or from about 0.02% to about 15% w/w.

Suitable pharmaceutically acceptable disintegrants include, but are not limited to, alginic acid, alginates, cellulose, cellulose derivatives, croscarmellose sodium, crospovidone, polacrillin potassium, sodium starch glycolate, starch, carboxymethyl starch, pregelatinized starch, or any combination of any of the foregoing. The disintegrant may be present in an amount ranging from about 0.5% to about 30% weight/weight (based upon 100% total weight of tablet), such as from about 1% to about 15% w/w, from about 0.5 to about 2% w/w, or from about 0.5 to about 1.5% w/w.

One or more glidants and/or lubricants may also be included in the immediate release tablet formulation of dofetilide.

Suitable glidants include, but are not limited to, colloidal silicon dioxide, talc, corn starch, or any combination of any of the foregoing. A preferred glidant is colloidal silicon dioxide. The glidant may be present in an amount in the range of about 0.07% to about 3% (based upon 100% total weight of the tablet).

Suitable pharmaceutically acceptable lubricants include, but are not limited to, sodium stearyl fumarate (SSF), magnesium stearate, corn starch, glyceryl behneate, zinc stearate, calcium stearate, stearic acid, hydrogenated vegetable oil, or any combination of any of the foregoing.

Preferred lubricants include magnesium stearate, stearic acid, or any combination of any of the foregoing.

The lubricant may be present in an amount in the range of about 0.1% to about 3% (based upon 100% total weight of the tablet).

The optional coating can be a functional coating or non-functional coating. The functional coating can be a coating which delays drug release to prevent the dose dumping effect. The functional coating can be a film coating or enteric coating which delays drug release to prevent a dose dumping effect.

The non-functional coating can be a film coating. Suitable film coatings includes those containing the following compendial excipients: microcrystalline cellulose, povidone, crospovidone, poloxamer 188, colloidal silicon dioxide, and magnesium stearate. An Opadry coating material (hypromellose, titanium dioxide, polyethylene glycol, Macrogol, talc and coloring agent) may be used for film coated tablets. The non-functional coating can be Opadry® II white, Opadry® II orange, Opadry® II brown, or Opadry® II yellow. Preferably, the non-functional coating is an immediate release coating and does not affect the release profile of the dofetilide.

The tablet may have a total weight of from about 50 to about 250 mg, such as from about 100 to about 200 mg. In one embodiment, the tablet has a total weight of 200 mg. In another embodiment, the tablet has a total weight of 100 mg.

The term content uniformity (CU) is defined as the variability in content between individual tablets derived from the same batch. CU is measured to ensure the consistency of dosage units, i.e., that each unit in a batch should have an active substance content within a narrow range around the target strength such that the batch falls within the specification limits set. CU is reported as relative standard deviation in percent (5% RSD).

In embodiments wherein a swallowable tablet is desired, the degree of particle compaction is controlled so that the resulting tablets have a hardness of about 1 to 30 kiloponds per square centimeter ($kp/cm^2$). "Hardness" is a term used in the art to describe the diametrical breaking strength as measured by conventional pharmaceutical hardness testing equipment, such as a Schleuniger Hardness Tester. In order to compare values across different size tablets, the breaking strength is normalized for the area of the break (which may be approximated as the tablet diameter times the thickness).

This normalized value, expressed in $kp/cm^2$, is sometimes referred in the art as tablet tensile strength. A general discussion of tablet hardness testing is found in Lieberman et al., Pharmaceutical Dosage Forms—Tablets, Volume 2, 2nd ed., Marcel Dekker Inc., 1990, pp. 213-217, 327-329.

In one embodiment, the tablet has a hardness in the range of about 250 to about 500 N, such as about 400±50 N.

In one preferred embodiment, the tablet has a hardness in the range of about 340 to 360±50 N (or about 290 to about 410 N).

The tablet may or may not comprise an outer coating as described below.

Optionally, one or more outer coatings may be applied over the tablet to provide protection during packaging and handling. Preferably, the coating is an immediate release coating and does not affect the release profile of the dofetilide.

Such outer coatings may comprise one or more tablet coating materials, such as gelatin, isomalt, monosaccharides, disaccharides, polysaccharides such as starch, cellulose derivatives, shellacs, polyhedric alcohols such as xylitol, mannitol, sorbitol, maltitol, erythritol, polyalkylene glycols, and any combination of any of the foregoing.

A variety of such outer coatings are known in the art, and any of these may be employed using techniques also known in the art.

Even uncoated, however, the present tablet advantageously has acceptable friability.

In the embodiment of the invention wherein the tablet hardness ranges from about 345±20N, friability levels are typically less than about 2%, preferably less than about 1%. A discussion of tablet friability is presented in USP 23 (1995) <1216> p. 1981.

Tikosyn refers to dofetilide capsules approved pursuant to U.S. New Drug Application No. 020931. Tikosyn is approved as 0.125, 0.25, and 0.5 mg capsules containing dofetilide.

Bioequivalence refers to when the tablet of the present invention has a 90% confidence interval for the mean $AUC_{0-t}$ and/or mean $AUC_{0-\infty}$ and/or $C_{max}$ relative to Tikosyn at the same dosage strength within 80% and 125%. AUC refers to the area under the plasma concentration time curve. $C_{max}$ refers to the maximum plasma concentration.

The pharmaceutical tablet of dofetilide can be manufactured by any of the method such as direct compression, dry granulation or wet granulation or fluidized technique or multi-particulates using an extrusion spheronization.

One method for manufacturing an immediate release tablet containing dofetilide or a pharmaceutically acceptable salt thereof, a diluent, a disintegrant, a glidant, and a lubricant comprises:
- a) adding a first portion of diluent to dofetilide or a pharmaceutically acceptable salt thereof and then adding a second portion of the diluent to form a first mixture;
- b) mixing the first mixture;
- c) a third portion of the diluent, the disintegrant, and the glidant to form a second mixture;
- d) adding a first portion of the second mixture to the first mixture and then adding the remaining portion of the second mixture to form a third mixture;
- e) mixing the third mixture;
- f) lubricating the third mixture by addition of a lubricant;
- g) compressing the lubricated mixture into a tablet; and
- h) optionally coating the tablet, wherein the coating is a functional or non-functional coating.

Another method for manufacturing an immediate release tablet containing dofetilide or a pharmaceutically acceptable salt thereof, a diluent, a disintegrant, a glidant, and a lubricant comprises:
- a) sifting all the ingredients including the dofetilide or a pharmaceutically acceptable salt thereof, diluent (e.g., microcrystalline cellulose), disintegrant (e.g., croscarmellose sodium), glidant (e.g., silicon dioxide), and lubricant (e.g., magnesium stearate);
- b) dividing the diluent into two equal parts, part 1 and part 2;
- c) adding approximately half of part 1 of the diluent and the dofetilide or a pharmaceutically acceptable salt thereof to a suitable blender and then adding the remaining half of part 1 of the diluent to the blender;
- d) mixing the step c) blend (for example, for 10 minutes at 15 rpm (such as 150 tumbles) to make a premix of dofetilide or a pharmaceutically acceptable salt thereof;
- e) sifting the step d) blend through a 40# sieve;
- f) co-sifting part 2 of the diluent, the disintegrant, and the glidant through 40# sieve;
- g) adding half of the step f) blend and the step e) blend to a suitable blender and then adding the remaining half of the step f) blend;
- h) mixing of the step g) blend in a suitable blender (for example, for 30 minutes at 15 rpm (such as 450 tumbles));
- i) lubricating the step h) blend with a lubricant;
- j) compressing the step i) blend to form a tablet (for instance, using suitable punches such as round/capsule/oval shaped punches and optionally with score line for dose adjustment); and
- k) optionally coating the tablet wherein the coating is a functional or non-functional coating.

Yet another method for manufacturing an immediate release tablet containing dofetilide or pharmaceutically acceptable salt thereof, microcrystalline cellulose, croscarmellose sodium, silicon dioxide, and magnesium stearate comprising:
- a) sifting of dofetilide or pharmaceutically acceptable salt thereof, microcrystalline cellulose, croscarmellose sodium, silicon dioxide, and magnesium stearate;
- b) dividing microcrystalline cellulose into two equal parts, part 1 and part 2;
- c) adding approximately half of the part 1 microcrystalline cellulose to the dofetilide or a pharmaceutically acceptable salt thereof and then adding the remaining half of the part 1 microcrystalline cellulose to a suitable blender;
- d) mixing the step c) blend (for example, for 10 minutes at 15 rpm (e.g., for 150 tumbles);
- e) sifting the step d) blend through a 40# sieve;
- f) co-sifting of the part 2 microcrystalline cellulose, croscarmellose sodium and silicon dioxide through a 40# sieve;
- g) adding half of the step f) blend to the sifted step e) blend and then adding the remaining half of the step f) blend to a suitable blender;
- h) mixing of the step g) blend in a suitable blender (e.g., for 30 minutes at 15 rpm (e.g., for 450 tumbles));
- i) lubricating the step h) blend with magnesium stearate;
- j) compressing the lubricated blend to form a tablet (for example, using suitable punches such as round/capsule/oval shaped punches and optionally with a score line for dose adjustment); and
- k) optionally coating the tablet wherein the coating comprises a functional or non-functional coating.

Yet another method for manufacturing a dofetilide immediate release tablet comprises:
- a) dry mixing dofetilide or a pharmaceutically acceptable salt thereof and one or more pharmaceutically acceptable excipients;
- b) dissolving (e.g., with stirring until a clear solution is obtained) one or more binders in an aqueous solvent or non-aqueous solvent or mixture thereof (e.g., a mixture of water and isopropanol (IPA)) to form a binder solution;
- c) granulating the blend of step a) with the binder-solution of step b);
- d) drying the granulation product of step c); and subsequently classify the granules;
- e) lubricating the granules of step d);
- f) compressing the mixture of step e) into a tablet (e.g., using round/capsule/oval shaped punches and optionally with a score line for dose adjustment).

An example of an aqueous solvent is water.

Examples of non-aqueous solvents include, but are not limited to, hydro-alcoholic solvent, isopropyl alcohol (IPA), methanol, ethanol benzyl alcohol, polyethylene glycol, propylene glycol, or a combination thereof. Other non-aqueous solvents include organic solvents such as dichloromethane or alcohols with 1 to 4 carbon atoms such as absolute ethanol, concentrated ethanol (96 vol %), methanol, isopropanol, ketones such as acetone or esters such as ethylacetate or mixtures thereof.

A preferred solvent is mixture of aqueous and non-aqueous solvents such as a mixture of water and isopropanol (IPA).

There are challenges of manufacturing tablets with low dose, and the inventor's surprisingly found a cost effective, commercially viable process for manufacturing dofetilide immediate release tablets even though the dose of dofetilide is in microgram levels by using a binder free composition, selecting a diluent which is having good compressibility, followed by direct compression.

The dofetilide immediate release tablet composition free of binder has the following advantages:
a) cost effective and commercially viable,
b) chemically stable,
c) comparative dissolution and bioequivalence profile to that of 'Tikosyn® capsule, and
d) optimum and robust hardness which is sufficient for handling.

In the another embodiment, the dofetilide immediate release tablet formulation contains total impurities less than 1.5% (based upon 100% total weight of the tablet) at accelerated stability conditions (i.e. storage at a temperature of 40° C. and a relative humidity 75%) for 1, 2, 3, or 6 months.

The examples below are illustrative embodiments and are merely exemplary. A person skilled in the art may make variations and modifications without deviating from the spirit and scope of the invention. All such modifications and variations are intended to be included within the scope of the claims.

Example 1: Preparation of Dofetilide Immediate Release Tablet by Direct Compression Manufacturing Process:

Step A: Microcrystalline cellulose was divided into two equal parts as part 1 and part 2, Step B: Approximately half of part 1 microcrystalline cellulose, dofetilide and then the remaining half of the part 1 microcrystalline cellulose were added to a suitable blender.

Step C: The blend in step B was mixed for 10 minutes at 15 RPM (150 tumbles) to make a premix of dofetilide.

Step D: The blend in step C was sifted through a suitable sieve (e.g., 40 mesh).

Step E: Part 2 of microcrystalline cellulose, croscarmellose sodium and colloidal silicon dioxide were co-sifted.

Step F: The blend in step E and blend in step D were added in a suitable blender.

Step G: The blend in step F was blended for 30 minutes at 15 RPM (450 tumbles) in a suitable blender.

Step H: Magnesium stearate was passed through sieve and added to step G blend.

Step I: The blend in step H was mixed in a suitable blender for 5 minutes at 15 RPM.

Step J: The lubricated blend of step I was compressed using suitable tools on a compression machine. Hardness was kept to achieve satisfactory friability and desired dissolution time.

Dissolution Studies:

The dissolution of the 0.5 mg dofetilide tablet of Example 1 was measured according to USP Type I (basket) at 100 rpm in 900 mL of (i) 0.001 M HCl, (ii) phosphate buffer at pH 6.8, or phosphate buffer at pH 4.5. The results are provided in Table 2.

TABLE 1

The composition of dofetilide immediate release tablets (direct compression)

| Sr. No. | Ingredients | 0.5 mg Quantity/unit | 0.5 mg % weight/weight | 0.25 mg Quantity/unit | 0.25 mg % weight/weight | 0.125 mg Quantity/unit | 0.125 mg % weight/weight |
|---|---|---|---|---|---|---|---|
| 1. | Dofetilide | 0.50 | 0.25 | 0.25 | 0.25 | 0.125 | 0.125 |
| 2. | Microcrystalline Cellulose (Avicel PH 102) | 189.495 | 94.75 | 94.75 | 94.75 | 94.875 | 94.875 |
| 3. | Croscarmellose Sodium (Ac-di-sol) | 6.0 | 3.0 | 3.0 | 3.0 | 3.0 | 3.0 |
| 4. | Colloidal Silicon dioxide (Aerosil) | 2.0 | 1.0 | 1.0 | 1.0 | 1.0 | 1.0 |
| 5. | Magnesium Stearate | 2.0 | 1.0 | 1.0 | 1.0 | 1.0 | 1.0 |
|  | Total | 200 mg | — | 100 mg | — | 100 mg | — |

TABLE 2

| Apparatus - USP Type I (Basket), medium - 0.001M HCl Speed - 100 RPM, Volume - 900 mL | | | | | |
|---|---|---|---|---|---|
| | 0.001 HCl | | 6.8 pH phosphate buffer | | 4.5 pH phosphate buffer | |
| Time Points (minutes) | % Drug released | % Relative Standard Deviation | % Drug released | % Relative Standard Deviation | % Drug released | % Relative Standard Deviation |
| 5 | 75 | — | 88 | 1.57 | 98 | 2.3 |
| 10 | 94 | — | 94 | 2.17 | 102 | 2.54 |
| 15 | 96 | — | 97 | 1.06 | 102 | 2.61 |
| 20 | 95 | — | 97 | 0.92 | 102 | 2.94 |
| 30 | 96 | — | 98 | 0.53 | 103 | 3.11 |
| 45 | 97 | — | 100 | 0.82 | 103 | 4.28 |

Conclusion:

From the dissolution study of the 0.5 mg dofetilide tablet, it was concluded that dissolution is more than 85% in 15 minutes in 0.1 N HCL, pH 6.8 Phosphate buffer and pH 4.5 phosphate buffer.

The dissolution profile of the 0.5 mg dofetilide tablets of Example 1 were measured in 0.001 M HCl dissolution medium and compare to that of 0.5 mg Tikosyn® Capsules. The results are shown in Table 3.

TABLE 3

| Time (Minutes) | Immediate release capsule (Tikosyn ®) 0.5 mg % Drug Release | 0.5 mg Dofetilide immediate release tablet of Example 1 % Drug Release |
|---|---|---|
| 5 | 73 | 75 |
| 10 | 94 | 94 |
| 15 | 96 | 96 |
| 20 | 96 | 95 |
| 30 | 95 | 96 |
| 45 | 96 | 97 |
| 60 | — | 98 |

Example 2: Preparation of Dofetilide Immediate Release Tablet by Wet Granulation

TABLE 4

| The composition of dofetilide immediate release tablets (wet granulation) | | | |
|---|---|---|---|
| Ingredients | Qty/unit 0.5 mg | Qty/unit 0.25 mg | Qty/unit 0.125 mg |
| Dofetilide | 0.5 | 0.25 | 0.125 |
| Microcrystalline Cellulose (Avicel PH 102) | 196.7 | 98.35 | 98.475 |
| Povidone | 0.1 | 0.05 | 0.05 |
| Croscarmellose Sodium (Ac-di-sol) | 2 | 1 | 1 |
| Colloidal Silicon dioxide (Aerosil) | 0.2 | 0.1 | 0.1 |
| Magnesium Stearate | 0.5 | 0.25 | 0.25 |
| Total weight of tablet | 200 mg | 100 mg | 100 mg |

Manufacturing Process:

Step A: Dofetilide, microcrystalline cellulose and croscarmellose sodium was dry mixed to obtain blend.

Step B: povidone was dissolved in a mixture of water and isopropanol (IPA) to obtain binder solution.

Step C: blend of Step A was granulated with the binder solution of Step B to obtain granules.

Step D: granules of Step C was dried and sifted (e.g., 30 mesh).

Step E: sifted granules of Step D was lubricated with magnesium stearate and

Step F: lubricated granules were compressed in to tablet using suitable tools on a compression machine. Hardness was kept to achieve satisfactory friability and desired dissolution time.

Stability Studies:

TABLE 5

| Stability Results of Dofetilide tablet - 0.5 mg Dofetilide Tablet - 0.5 mg Packing: 60 CC HDPE with CR cap | | | | |
|---|---|---|---|---|
| Tests | Tentative Limits | Initial | 1 Month 40° C./75% | 2 Month 40° C./75% |
| Assay (%) | 90.0-110.0% | 97.6 | 99 | 98.3 |
| Related Substance | | | | |
| Imp A | RRT-0.85 NMT 0.5% | 0.02 | 0.07 | 0.09 |
| N-Oxide | RRT-1.27 NMT 1% | 0.06 | 0.03 | 0.04 |
| Unknown 1 | RRT-1.57 | ND | 0.11 | 0.08 |
| Unknown 2 | RRT-1.72 | ND | 0.07 | 0.07 |
| Unknown 3 | RRT-0.27 | ND | ND | ND |
| Single Max Unknown Impurity (%) | NMT 0.5% | ND | 0.11 | 0.08 |
| Total Impurity (%) | NMT 1.5% | 0.08 | 0.28 | 0.28 |
| % Drug Dissolve | | | | |
| 5 min | | 92 | 86 | 66 |
| 10 min | | 100 | 96 | 100 |
| 15 min | NLT 85% | 101 | 97 | 102 |
| 20 min | | 102 | 97 | 101 |
| 30 min | | 102 | 97 | 102 |
| 45 min | | 102 | 97 | 102 |

N-oxide impurity: Methanesulfonaide, N-[4-[2-[methyl [2-[4-[(methylsulfonyl)amino]phenoxy]ethyl]amino]ethyl] phenyl]-N-oxide Impurity A: N-[4-(2-(2-[4-(methanesulfonamido) phenoxy]ethylamino)ethyl)phenyl]methane sulfonamide Observation:

All Impurities are found well within limit up to 2 M at accelerated condition.

CONCLUSION 2 month accelerated stability data of the 0.5 mg dofetilide tablets of Example 1 were found acceptable with respect to the assay, related substance and dissolution. All impurities are well within the limit. Total impurity increases to 0.28% after storage for 2 months under accelerated storage conditions. No change in dissolution.

All references cited herein are incorporated by reference.

We claim:

1. An immediate release tablet formulation comprising:
   a) dofetilide or a pharmaceutically acceptable salt thereof in an amount in the range of 0.05 to about 10% w/w;
   b) a pharmaceutically acceptable diluent comprising microcrystalline cellulose in an amount ranging from about 5% to about 98% w/w;
   c) a pharmaceutically acceptable disintegrant comprising croscarmellose sodium in an amount ranging from about 1% to about 20% w/w;
   d) a glidant comprising colloidal silicon dioxide in an amount ranging from about 0.07% to about 3%; and/or a lubricant comprising magnesium stearate in an amount ranging from about 0.1% to about 3%; and
   e) optionally a coating comprising a functional or non-functional coating, wherein the formulation releases at least 80 wt. % of the dofetilide or pharmaceutically acceptable salt thereof from the tablet within 15 minutes.

2. The tablet formulation according to claim 1, wherein dofetilide or a pharmaceutically acceptable salt thereof is present in the range of 0.1 to 0.5% w/w of the tablet formulation.

3. The tablet formulation according to claim 1, wherein dofetilide or a pharmaceutically acceptable salt thereof is present in the range of 0.1 mg to 0.5 mg.

4. The tablet formulation according to claim 1, wherein the formulation further comprises at least one pharmaceutically acceptable binder in an amount ranges between 0.02-20% w/w, and optionally a coating.

5. The tablet formulation according to claim 1, wherein the formulation is coated.

6. The tablet formulation according to claim 1, wherein the tablet is used for treating arrhythmia in mammals.

7. The immediate release tablet formulation according to claim 1, wherein said formulation is prepared by the method comprising direct compression, dry granulation, wet granulation, a fluidized technique or extrusion spheronization.

8. The tablet formulation according to claim 1, wherein at least 85 wt. % of dofetilide or a pharmaceutically acceptable salt thereof in the tablet formulation is dissolved from the tablet within 15 minutes as measured according to USP Type I (basket) at 100 rpm in 900 mL of 0.001 M HCl.

9. An immediate release tablet formulation comprising
   a) dofetilide or a pharmaceutically acceptable salt thereof in an amount in the range of 0.05 to about 10% w/w;
   b) a pharmaceutically acceptable diluent comprising microcrystalline cellulose in an amount ranging from about 5% to about 98% w/w;
   c) a pharmaceutically acceptable binder comprising povidone or/and HPMC in an amount ranging from about 0.02-30% w/w %;
   d) a pharmaceutically acceptable disintegrant comprising croscarmellose sodium in an amount ranging from about 1% to about 20% w/w;
   e) a pharmaceutically acceptable glidant comprising colloidal silicon dioxide in an amount ranging from about 0.07% to about 3% and/or a pharmaceutically acceptable lubricant comprising magnesium stearate in an amount ranging from about 0.1% to about 3%; and
   f) optionally a coating comprising a functional or non-functional coating, wherein the formulation releases at least 80 wt. % of the dofetilide or pharmaceutically acceptable salt thereof from the tablet within 15 minutes.

* * * * *